United States Patent [19]
Jones et al.

[11] 4,325,883
[45] Apr. 20, 1982

[54] PROCESS FOR BLEACHING NATURALLY-OCCURRING OILS AND FATS

[75] Inventors: Keith Jones, Wirral; Francis R. M. McDonnell, South Wirral; Stuart N. Morgan, Liverpool; David W. Thornthwaite, Wirral, all of England

[73] Assignee: Lever Brothers Company, New York, N.Y.

[21] Appl. No.: 200,250

[22] Filed: Oct. 24, 1980

[30] Foreign Application Priority Data

Oct. 25, 1979 [GB] United Kingdom ............... 37130/79

[51] Int. Cl.$^3$ ............................................. C07C 27/10
[52] U.S. Cl. .................................................... 260/423
[58] Field of Search ................................ 260/406, 423

[56] References Cited

U.S. PATENT DOCUMENTS

| | | | |
|---|---|---|---|
| 1,834,866 | 12/1931 | Pungs | 260/423 |
| 2,369,757 | 2/1945 | Schmidt | 260/423 |
| 3,996,259 | 12/1976 | Lee et al. | 562/533 |
| 4,198,285 | 5/1980 | Carlos | 260/406 |

OTHER PUBLICATIONS

"Neuzeitliche Technologie Der Fette und Fettprodukte", p. 773, referred to a reference 317 which in turn is Japanese Patent 3633/1950.
Chemical Abstracts 46 9872i on Japanese Patent.
Angewandte Chemie, vol. 16, No. 8, Aug. 1977, pp. 493–508.
"Application of Phase-Transfer Catalysis in Organic Synthesis", from Aldrichimica Acta, vol. 9, No. 3, 1976.
"Phase Transfer Catalyzed Oxidations of Alcohols and Amines by Aqueous Hypochlorite", from Tetrahedron Letters No. 20, pp. 1641-1644, 1976.

*Primary Examiner*—John F. Niebling
*Attorney, Agent, or Firm*—James J. Farrell; Melvin H. Kurtz

[57] ABSTRACT

A process for bleaching an oil or fat is disclosed wherein a polar bleaching agent is employed in the presence of a phase transfer catalyst.

13 Claims, No Drawings

PROCESS FOR BLEACHING NATURALLY-OCCURRING OILS AND FATS

The present invention relates to a process for bleaching naturally-occurring oils and fats, and has especial applicability to the bleaching of certain oils and fats used as raw materials in soap-making, for example, palm oil, coconut oil, tallow and rice bran oil.

These oils are generally fairly highly coloured and for aesthetic reasons require bleaching before they can be used in soap-making. Some commercially significant vegetable oils are highly coloured owing to the presence of chromophoric impurities: one which is particularly highly coloured is palm oil, which has been estimated to contain up to about 0.2% of the red pigment beta-carotene. Palm oil is derived from the pericarp (the thick fibrous outer layer) of the fruit of the oil palm, *elaeis guineensis,* and contains about 48% of hexadecanoic (palmitic) acid and about 38% of oleic acids. Decolorisation of palm oil is currently carried out using an adsorbent solid material, sulphuric acid-activated Fuller's earth, and high levels of this material (up to about 12% by weight) are required for adequate bleaching, both because of the high concentration of coloured impurities and because of the hydrophobic nature of the oil. The earth bleach adsorbs approximately its own weight of oil, which is lost, so that the current process is expensive both in terms of catalyst consumption and in terms of oil loss. The disposal of the spent earth also presents a problem.

Sal and rice bran oils, which are important raw materials for soap in the Indian sub-continent, are currently bleached with chlorine dioxide. This is a hazardous reagent which can present process control difficulties. Neem, another important Indian oil, is bleached using sodium chlorite and mild acid.

It has now been found that oils and fats can be successfully bleached with milder, aqueous bleaching agents such as hypochlorite and peroxide, in the presence of a phase transfer catalyst.

The action of polar bleaching agents such as hypochlorite on these oils in the absence of a catalyst is slow and incomplete because of the hydrophobic nature of the oils. The reaction (oxidation or reduction of the coloured impurity) probably takes place in the organic phase and the bleaching agent in the aqueous phase cannot easily penetrate the organic phase to reach the reaction site.

A phase transfer catalyst is a charged compound which also possesses significant oil solubility. Such a material can assist in a reaction between a charged species and a hydrophobic substrate in an organic phase by carrying the charged species, for example, as an ion pair, into the organic phase.

The use of phase transfer catalysts for oxidising hydrophobic substances such as amines, amides, alcohols and organic compounds containing an activated doubled bond is described in an article in Tetrahedron Letters, 1976, 20, p. 1641-1644 and in U.S. Pat. No. 3,996,259. Other articles on phase transfer catalysis appear in Angewandte Chemie International 1977, 16, p. 493-505; Aldrichimica Acta 1976, 9, p. 35-45; and J. Chem. Ed. 1978, 55, p. 429-433.

Clearly, a phase transfer catalyst must be of appropriate charge type for the polar reaction species involved. For a bleaching process involving an anionic species such as hypochlorite ion, hydroperoxide ion or a peroxo acid anion, the catalyst cannot itself be anionic, and an anionic surface-active agent will have no phase-transfer catalytic effect on such a reaction.

Japanese Pat. No. 3633/1950 to Nojima and Ishikawa discloses a process for the decolorisation of rice bran oil in which a small proportion of the oil is either sulphonated or saponified and the oil is then bleached with hydrogen peroxide. The sulphonate or carboxylate present here is anionic and is thus not of the appropriate charge type to behave as a phase transfer catalyst.

In its broadest aspect the present invention provides a process for bleaching an oil or fat, which comprises treating the oil or fat with a polar bleaching agent in the presence of a phase transfer catalyst.

The invention is particularly relevant to the bleaching of naturally-occurring oils, especially those used in soap-making. Examples of vegetable oils to which the invention is applicable are palm oil, coconut oil, bay tree leaf oil, sal oil, neem oil and rice bran oil; an example of an animal product is tallow.

The bleaching agent should be selected according to the chromophoric impurity to be removed. In general, the chromophores present in the oils used for soap-making, for example, the beta-carotene in palm oil and the chlorophyll in sal oil, are most easily dealt with by oxidation, and therefore oxidative bleaches are appropriate. Examples of suitable oxidative bleaches are salts of hypochlorous acid, and most preferably sodium hypochlorite; peroxyacids such as peracetic acid also give excellent results. Other oxidative bleaching agents that may be used include "hyprox" (a sodium hypochlorite/-hydrogen peroxide mixture), hydrogen peroxide itself, chlorites, organic chloramines and chlorinated trisodium phosphate.

The use of reductive bleaching agents such as dithionite and borohydride is also within the scope of the invention. These are appropriate when the coloured impurity is reducible, rather than oxidisable, to form a colourless product, for example, fluorenone to fluorenol or azo dyes to diamino compounds.

The bleaching agent will preferably be present in the reaction mixture in an amount of from 0.5 to 10% by weight based on the weight of the oil or fat, the optimum amount depending on the bleaching agent and the oil or fat used. Sodium hypochlorite is preferably used in an amount of from 1.5 to 8.0% by weight, preferably 2 to 4.5% by weight for palm oil and 5 to 7.5% by weight for sal or rice bran oil. Peracetic acid is advantageously used in an amount of from 3 to 10% by weight, and hydrogen peroxide in the same amount, the percentages being by weight of the oil or fat.

The phase transfer catalysts used according to the present invention will in general be cationic for compatibility with anionic bleaches such as hypochlorite, hydrogen peroxide or peracetic acid, and quaternary ammonium compounds and quaternary phosphonium compounds are especially suitable, quaternary ammonium compounds being preferred on grounds of cost and availability.

These quaternary ammonium compounds preferably have the general formula $$R_1R_2R_3R_4N^+X^-$$

in which $R_1R_2R_3$ and $R_4$ are $C_1$ to $C_{22}$ alkyl groups, the total number of carbon atoms in the R groups being at least 16, and $X^-$ is a monovalent anion, especially halide, or 1/m of an m-valent anion.

For a given total number of carbon atoms in the R groups, four intermediate length chains give better results than one or two long ones. Tetra-n-octyl ammonium bromide is an outstanding efficient phase transfer catalyst, and tetra-n-butyl ammonium chloride is also effective, but less so than the tetra-$C_8$ compound.

Compounds of the type in which two of the R groups are $C_1$ to $C_3$ alkyl, especially methyl, and the other two $C_{10}$ to $C_{22}$ are efficient, cost-effective catalysts. An example of this type is di(hydrogenated tallow alkyl) dimethyl ammonium chloride, available commercially as Arquad (Trade Mark) 2HT.

Finally, quaternary ammonium compounds having one long chain and three lower alkyl groups, such as cetyl trimethyl ammonium chloride, are also useful as phase transfer catalysts according to the invention.

The phase transfer catalyst is preferably used in an amount of from 0.2 to 10 mole %, based on the bleaching agent, especially 0.5 to 4 mole %.

The reaction temperature is preferably from 30° to 80° C., from 45° to 60° C. being especially preferred for palm oil, and slightly higher temperature (up to 75° C.) being preferred for sal and rice bran oils.

The preferred pH is from 7 to 11, preferably from 8.5 to 9.5.

As well as increasing the rate of bleaching, the presence of the phase transfer catalyst gives a more completely bleached product. It has been found, for example, that palm oil of sufficiently low colour level for soap-making cannot be obtained using hypochlorite unless a phase transfer catalyst is used.

The process of the invention may be carried out as a two-stage operation. In the first stage the oil (brought to the preferred temperature of 45° to 60° C., for example by steam heating), the bleach and the catalyst may be mixed together in a suitable bleach vessel. The reacted mixture may then be transferred to a settler or a rotating disc separator, where the aqueous phase can be washed out with 20% brine and the bleached oil drawn off for deodorisation (if necessary) and fed to, for example, soap-making plants.

If the oil to be bleached has a high concentration of free fatty acids, as does rice bran oil, it may be advantageous either to distil off these volatile acids or to esterify them (for example, using methanol or ethanol with toluene sulphonic acid as catalyst) before bleaching. This is however by no means essential.

The following Examples illustrate the invention.

EXAMPLE 1

Palm oil (25 g) and water (25 g) were placed in a flask together with sodium hypochlorite (2% by weight of the palm oil) and tetra-n-butyl ammonium hydroxide (0.7% by weight of the palm oil). The mixture was then adjusted to pH 9 and the flask and contents placed in a constant temperature water bath to give a reaction temperature of 30° C.

The reaction was continued for one hour, after which time sodium sulphite was added to remove any unused sodium hypochlorite. The bleached palm oil was then extracted with hexane with the addition of salt solution to aid phase separation. The solvent was removed under vacuum, and samples of the bleached palm oil were evaluated in a qualitative manner (visually) and quantitatively (by measurement of the optical density at 446 nm of a 1% solution in hexane using a Pye-Unicam SP 800 spectrophotometer). The results are shown in Table 1.

TABLE 1

| Sample | Colour | Optical density |
|---|---|---|
| Untreated palm oil | Bright orange | 1.04 |
| Palm oil bleached without phase transfer catalyst | Pale yellow | 0.20 |
| Palm oil bleached with phase transfer catalyst | White | 0.01 |

The above Example illustrates the increased effectiveness of bleaching reactions applied to palm oil which can be achieved by use of a phase transfer catalyst.

EXAMPLE 2

Palm oil (100 g) was added to a flask containing 100 g of an aqueous solution of sodium hypochlorite (1% by weight based on the palm oil). Tetra-n-butyl ammonium hydroxide (10 mole % based on the bleach, 0.35% by weight based on the oil) was added to the mixture and the contents of the flask were stirred at 500–600 r.p.m. at 30° C. for one hour.

A control experiment using identical reaction conditions, except that the catalyst was omitted, was also carried out for comparison purposes.

After the reaction time of one hour had elapsed a solution of sodium sulphite was added to destroy any excess of bleach, the mixture was transferred to a separating funnel and partitioned between ether and saturated sodium chloride solution. The ether layer was removed, dried over anhydrous magnesium sulphate, filtered and concentrated under reduced pressure.

Measurements of the optical density of the bleached and unbleached oils were made at 446 nm on a 1% oil solution in hexane, using a Pye-Unicam SP 800 spectrophotometer. The results were as follows:

| | Optical density |
|---|---|
| Unbleached oil | 1.04 |
| Bleached oil (uncatalysed) | 0.68 |
| Bleached oil (catalysed) | 0.48 |

The "percentage of bleaching" was calculated according to the following equation:

$$\% \text{ bleaching} = \frac{\text{optical density of unbleached oil} - \text{optical density of bleached oil}}{\text{optical density of unbleached oil}}$$

and was found to be 34.6% for the uncatalysed sample and 53.8% for the catalysed sample.

EXAMPLE 3

The procedure of Example 2 was repeated using various bleach concentrations, reaction temperatures and reaction times. The optical densities were measured, and the percentages of bleaching calculated, as in Example 2. The results are shown in Table 2, from which the improvement obtained by using the phase transfer catalyst can readily be seen.

TABLE 2

| | Bleach concn. % | Reaction temp(°C.) | Reaction time (h) | pH | % Bleaching uncatalysed | % Bleaching catalysed |
|---|---|---|---|---|---|---|
| (a) | 1 | 30 | 1 | 9 | 36.2 | 52.9 |
| (b) | 1 | 50 | 1 | 9 | 20.6 | 32.4 |
| (c) | 1 | 30 | 2 | 9 | 34.0 | 44.0 |

TABLE 2-continued

| | Bleach concn. % | Reaction temp(°C.) | Reaction time (h) | pH | % Bleaching uncatalysed | catalysed |
|---|---|---|---|---|---|---|
| (d) | 1 | 30 | 3 | 9 | 30.3 | 67.4 |
| (e) | 2 | 30 | 1 | 9 | 88.5 | 100.0* |

*The optical density of the bleached oil was outside the detection limits of the machine (± 0.01), although the oil was not water-white.

EXAMPLE 4

The procedure of Example 2 was repeated using peracetic acid instead of sodium hypochlorite. The concentration of peracetic acid used was 2% by weight based on the oil, the catalyst concentration was 10 mole % based on the peracetic acid (0.68% by weight based on the palm oil), the reaction time was one hour, the reaction temperature 50° C., and the pH 9. A corresponding uncatalysed run was also carried out.

Optical densities were measured as in Example 2 and were as follows:

| | Optical density |
|---|---|
| Unbleached oil | 1.04 |
| Bleached oil (uncatalysed) | 0.74 |
| Bleached oil (catalysed) | 0.03 |

The percentages of bleaching were thus 28.8% (uncatalysed) and 97.1% (catalysed).

EXAMPLE 5

The experiment of Example 4 was repeated at bleach concentrations of 1% and 2%, other conditions remaining the same. The results are shown in Table 3.

TABLE 3

| | Bleach concn.% | % Bleaching uncatalysed | catalysed |
|---|---|---|---|
| (a) | 1 | 29.7 | 83.2 |
| (b) | 2 | 28.4 | 97.5 |

EXAMPLE 6

The procedure of Example 2 was repeated using sodium chlorite instead of sodium hypochlorite. The bleach concentration was 1% by weight based on the palm oil, the catalyst concentration was 10 mole % based on the bleach (0.29% by weight based on the palm oil), the reaction time was one hour, the reaction temperature 30° C. and the pH was 9. A comparison uncatalysed run was also carried out. Optical densities and percentages of bleaching were as follows:

| | Optical density | % bleaching |
|---|---|---|
| Unbleached oil | 1.04 | — |
| Bleached oil (uncatalysed) | 1.04 | 0 |
| Bleached oil (catalysed) | 0.86 | 17.3 |

It will be seen that no measurable bleaching occurred at all unless the phase transfer catalyst tetra-n-butyl ammonium hydroxide was present.

EXAMPLE 7

The procedure of Example 2 was repeated using hydrogen peroxide instead of sodium hypochlorite. The bleach concentration was 1% by weight based on the palm oil, the catalyst concentration was 10 mole % based on the bleach (0.76% by weight based on the palm oil), the reaction time was one hour and the pH was 10. The results are given in Table 4.

TABLE 4

| Reaction temp(°C.) | Optical density uncatalysed | catalysed | % bleaching uncatalysed | catalysed |
|---|---|---|---|---|
| 30 | 1.0 | 0.93 | 3.8 | 10.6 |
| 75 | 0.83 | 0.52 | 20.2 | 50.0 |

At both temperatures the use of the catalyst represented a considerable improvement over the uncatalysed reaction, but substantially better results were obtained at 75° C.

EXAMPLE 8

A series of experiments was carried out using the procedure of Example 2, to illustrate the effect of reaction temperature on the colour of the bleached oil in the palm oil/sodium hypochlorite system. In this Example the catalyst used was Arquad (Trade Mark) 2HT (di(hydrogenated tallow alkyl) dimethyl ammonium chloride). The concentration of sodium hypochlorite used was 2.5% based on the palm oil, the catalyst concentration was 2.5 mole % based on the bleach, the pH was 9 and the reaction time was 2 hours. The results are shown in Table 5. The colour was measured using a Lovibond tintometer: R denotes red, Y yellow and B blue. The cell length was 5¼ inches (133.4 mm). The unbleached oil had a colour equivalent to 120 R 273 Y in a Lovibond 133.4 mm cell; this value was obtained by scaling-up a reading taken in a smaller cell.

TABLE 5

| Temperature °C. | Lovibond colour uncatalysed | catalysed |
|---|---|---|
| 30 | 5R 43Y | 3.4R 30Y |
| 40 | 4R 38Y 0.1B | 2R 20Y |
| 50 | 2.8R 32Y | 1.5R 15Y |
| 70 | 1R 28Y | 1R 14Y |

EXAMPLE 9

Using the procedure of Example 2, a series of experiments was carried out to illustrate the effect of hypochlorite concentration on the colour of the bleached palm oil. The catalyst used was Arquad (Trade Mark) 2HT, the pH was 9, and the temperature was 50° C. The results are set out in Table 6.

TABLE 6

| Bleach concn. (% based on oil) | Catalyst concn. (mole % based on bleach | Reaction time (hours) | Lovibond colour uncatalysed | | catalysed | |
|---|---|---|---|---|---|---|
| 2.0 | 2.5 | 1 | 5.7R | 51.5Y | 2.6R | 15Y |
| 2.5 | 2.5 | 1 | 3.8R | 39Y | 2.1R | 25Y |
| 3.0 | 2.5 | 1 | 3.3R | 30Y | 2.3R | 20Y |
| 6.0 | 1.0 | 2 | 2R | 17Y | 1R | 8Y |

All catalyst levels gave good results.

EXAMPLE 10

The experiments of Example 9 were repeated with varying levels of catalyst to determine the effect of this variable on the product colour. The results are shown in Table 7.

TABLE 7

| Hypochlorite concn. (% based on oil) | Catalyst conc. (mole % based on bleach) | Reaction time (hours) | Lovibond colour uncatalysed | | Lovibond colour catalysed | |
|---|---|---|---|---|---|---|
| (a) 2.0 | (i) 2.5 | 1 | 5.7R | 51.5Y | 2.6R | 15Y |
| | (ii) 5.0 | 1 | 7.7R | 61Y | 2.9R | 21Y |
| (b) 2.5 | (i) 1.0 | 1 | 5R | 40Y | 3R | 22Y |
| | (ii) 2.5 | 1 | 3.8R | 39Y | 2.1R | 25Y |
| | (iii) 4.0 | 1 | 7.1R | 60Y | 2.9R | 22Y |
| | (iv) 5.0 | 1 | 7.4R | 65Y | 3.3R | 30Y |
| (c) 3.0 | (i) 1.0 | 1 | 3R | 22Y | 2.4R | 15Y |
| | (ii) 2.5 | 1 | 3.1R | 20Y | 2.1R | 15Y |
| | (iii) 3.0 | 1 | 4R | 24Y | 2.3R | 13Y |
| (d) 6.0 | 1.0 | 2 | 2R | 17Y | 1R | 8Y |

In all cases the product produced by the catalysed process was significantly better than that produced by the corresponding uncatalysed process.

EXAMPLE 11

Using the procedure of Example 2, the products produced by the hypochlorite bleaching of palm oil in the presence of three phase transfer catalysts were compared. The hypochlorite concentration was 2.5% based on the oil, the reaction temperature was 50° C., the reaction time was one hour, and the pH was 9.0. The results are shown in Table 8.

TABLE 8

| Catalyst | Mole % concn. (based on bleach) | Lovibond colour uncatalysed | | Lovibond colour catalysed | |
|---|---|---|---|---|---|
| Arquad (Trade Mark) 2 HT | 2.5 | 3.8R | 39Y | 2.1R | 25Y |
| Tetra-n-octyl ammonium bromide | 1.0 | 3R | 16Y | 1.7R | 11Y |
| Tetra-n-butyl ammonium hydroxide | 10.0 | 10R | 32Y | 5R | 33Y |

This test demonstrates the superiority of tetra-n-octyl ammonium bromide. The product obtained using Arquad (Trade Mark) 2 HT was, however, acceptable.

EXAMPLE 12

A series of experiments was carried out, using the procedure of Example 2, to determine the influence of pH and reaction time on the colour of palm oil bleached by the hypochlorite/Arquad (Trade Mark) 2 HT system. The bleach concentration was 2.5% based on the oil and the catalyst concentration was 2.5 mole % based on the bleach. Table 9 shows the effect of reaction time at reaction temperature 50° C. and pH 9.

TABLE 9

| Reaction time (hours) | Lovibond colour uncatalysed | Lovibond colour catalysed |
|---|---|---|
| 1 | 3.8R 39Y | 2.1R 25Y |
| 2 | 2.8R 32Y | 1.5R 15Y |
| 2 | 3R 30Y | 1.4R 13Y |
| 3 | 3R 34Y | 1.6R 19Y |

Table 10 shows the effect of pH at one hour reaction time and reaction temperature 50° C.

TABLE 10

| pH | Lovibond colour uncatalysed | Lovibond colour catalysed |
|---|---|---|
| 8 | 23R 62Y | 16R 60Y |
| 9 | 3.8R 39Y | 2.1R 25Y |
| 10 | 7.9R 40Y | 2.5R 40Y |
| 11 | 5.2R 26Y | 4R 23Y |

The results indicate that at 50° C. a reaction time of two hours and a pH of 9 represent optimum conditions.

EXAMPLE 13

An experiment was carried out to demonstrate that the decomposition of the pigment carotene (the main coloured impurity in palm oil) by hypochlorite is accelerated by Arquad (Trade Mark) 2 HT.

The pigment was dissolved in petrol and reacted with sodium hypochlorite (0.4 M) in the presence of 0.0025 M Arquad (Trade Mark) 2 HT at 30° C. and pH 11.6. A control experiment was also run in which the catalyst was omitted. The reactions were carried out in dark vessels to avoid photobleaching. The petrol solution was sampled at regular intervals and the pseudo-first order reaction rate constants were found to be $8.14\times10^{-6}$ $sec^{-1}$ for the uncatalysed case and $4.07\times10^{-4}$ $sec^{-1}$ in the catalysed case, the latter representing an approximately 50-fold rate enhancement.

EXAMPLE 14

Using the procedure of Example 2, samples of palm oil were bleached with peracetic acid and "hyprox" (sodium hypochlorite/hydrogen peroxide), both with and without catalyst. The reaction time was one hour and the catalyst was Arquad (Trade Mark) 2 HT in each case. The results are shown in Table 11.

TABLE 11

| Bleach | Bleach concn. (% on oil) | Catalyst concn. (mole % on bleach) | Temp °C. | pH | Lovibond colour uncatalysed | Lovibond colour catalysed |
|---|---|---|---|---|---|---|
| Peracetic acid | 2 | 2.5 | 50 | 9 | 52.5R 126Y | 47R 20Y |
| Peracetic acid | 3 | 2.5 | 60 | 9 | 47R 120Y | 25R 35Y |
| Peracetic acid | 4 | 2.5 | 60 | 9 | 16R 25Y | 16R 24Y |
| Peracetic acid | 5 | 2.5 | 60 | 10 | 21R 20Y | 19R 17Y |
| Peracetic acid | 4 | 4.0 | 60 | 10 | 16R 146Y | 5R 21Y |
| Peracetic acid | 5 | 2.5 | 60 | 9 | 21R 20Y | 19R 17Y |
| Sodium hypochlorite plus hydrogen peroxide | 2.5 / 0.25 | 2.5 | 50 | 9 | 41R 20Y | 2.3R 25Y |

It was found that peracetic acid was a considerably less effective bleaching agent than hypochlorite for decolourising palm oil. The "hyprox" gave results comparable with those obtained using hypochlorite alone.

EXAMPLE 15

Using procedures analogous to that of Example 2, samples of coconut oil were bleached with sodium hypochlorite and "hyprox" in the presence of Arquad (Trade Mark) 2 HT. The reaction temperature was 45° C. in each case.

Table 12 shows the results obtained using a sample of good quality coconut oil of Lovibond colour 3.5R 11Y. The catalyst concentration was 2.5 mole % based on bleach in each case.

TABLE 12

| Bleach | Bleach concn. (% on oil) | Time (hours) | pH | Lovibond colour uncatalysed | | Lovibond colour catalysed | |
|---|---|---|---|---|---|---|---|
| NaOCl | 2.5 | 1 | 9 | 1R | 4Y | 1R | 3Y |
| NaOCl | 5.0 | 1 | 9 | 0.5R | 4Y | 0.5R | 3Y |
| NaOCl + $H_2O_2$ | 2.5 / 0.5 | 1 | 9 | 0.3R | 2Y | 0R | 2Y |

Table 13 shows the results obtained using a sample of Philippines coconut oil of Lovibond colour 10R 50Y.

TABLE 13

| Bleach | Bleach concn. (% on oil) | Catalyst concn. (mole % on bleach) | Time (hours) | pH | Lovibond colour uncatalysed | | Lovibond colour catalysed | |
|---|---|---|---|---|---|---|---|---|
| NaOCl | 2.5 | 2.5 | 1 | 9 | 3R | 4Y | 2R | 3Y |
| NaOCl | 2.5 | 2.5 | 2 | 9 | 1.5R | 3Y | 1.5R | 2Y |
| NaOCl | 2.5 | 2.5 | 1 | 4 | 0R | 3.5Y | 0R | 2Y |
| NaOCl | 2.5 | 2.5 | 1 | 11 | 5R | 7Y | 5R | 5Y |
| NaOCl + $H_2O_2$ | 2.5 / 0.5 | 2.5 | 1 | 9 | 1.5R | 3Y | 0.5R | 3Y |
| NaOCl | 2.5 | 5.0 | 1 | 9 | 3R | 4Y | 0.9R | 3Y |

Even with the more highly coloured Philippines oil most of of the bleached samples were of soap-making quality.

EXAMPLE 16

Using a procedure analogous to that of Example 2, a sample of Grade 4 tallow was bleached with sodium hypochlorite (2.5% based on the tallow) in the presence and absence of Arquad (Trade Mark) 2 HT (2.5 mole % based on the bleach). The temperature was 50° C., the reaction time was 2 hours and the pH was 9. The Lovibond colours of the tallow before and after bleaching were as follows:

| | | | |
|---|---|---|---|
| Untreated | 52.5R | 210Y | 15.2B |
| Bleached (uncatalysed) | 8.6R | 62Y | 2.9B |
| Bleached (catalysed) | 5.6R | 23Y | 2.6B |

The use of the catalyst thus effected a considerable improvement in the quality of the product.

EXAMPLE 17

A sample of bay tree leaf oil was bleached, according to a procedure analogous to that of Example 2, with sodium hypochlorite (6% based on the oil) in the presence and absence of Arquad (Trade Mark) 2 HT (2.5% based on the bleach), at 60° C. and pH 9 for one hour. The Lovibond colours of the oil were as follows:

| | | |
|---|---|---|
| Uncatalysed | 43Y | 325Y |
| Catalysed | 37.8Y | 36Y |

EXAMPLE 18

Samples of sal oil were bleached, by a procedure analogous to that of Example 2, with sodium hypochlorite, in the presence and absence of Arquad (Trade Mark) 2 HT, at 50° C. and pH 11. The catalyst concentration was 1 mole % based on the bleach. The results are shown in Table 14.

TABLE 14

| Bleach concn. (% of oil) | Reaction Time (hours) | Lovibond colour uncatalysed | | Lovibond colour catalysed | |
|---|---|---|---|---|---|
| 7.5 | 2 | 1.5R | 6Y | 1.5R | 5.6R |
| 6 (3 additions of 2% at 45 minute intervals) | 2.25 | 10.5R | 52Y | 3.1R | 30Y |

A commercial sample that had been bleached with chlorine dioxide had a Lovibond colour equivalent to 50R 36Y in the 133.4 mm cell (scaled-up from a reading taken in a smaller cell). The phase-catalysed bleached product thus represents a substantial improvement.

EXAMPLE 19

Samples of hardened rice bran oil were bleached, using a procedure analogous to that of Example 2, with sodium hypochlorite in the presence and absence of Arquad (Trade Mark) 2 HT. The reaction time was 2 hours. Since rice bran oil is extremely strongly coloured, Lovibond colours in this Example were measured using a 5 mm (¼-inch) cell. The results are shown in Table 15.

TABLE 15

| Bleach level (% on oil) | Catalysed level (weight % on oil) | Catalysed level (Mole % on bleach) | Temp °C. | Lovibond colour Uncatalysed | Lovibond colour Catalysed | | Total colour (5R + Y) Uncatalysed | Total colour (5R + Y) Catalysed |
|---|---|---|---|---|---|---|---|---|
| 5 | 0.935 | | 50 | 5.1R 41Y | 6R | 30Y | 66.5 | 60 |
| 7.5 | 0.56 | | 50 | 4.4R 74Y | 4R | 37Y | 96 | 57 |
| 7.5 | 1.40 | | 50 | 4.4R 74Y | 4.7R | 21Y | 96 | 44.5 |
| 7.5 (3 additions of 2.5% at 45-minute intervals) | 0.45 | | 50 | — | 4.2R | 25Y | — | 46 |
| | 0.45 | | 60 | — | 5R | 23Y | — | 48.5 |
| 4.5 (3 additions of 1.5% at | 0.27 | | 50 | — | 4R | 27Y | — | 47 |
| | 0.27 | | 60 | — | 4R | 21Y | — | 51 |

TABLE 15-continued

| Bleach level (% on oil) | Catalysed level (weight % on oil) | Catalysed level (Mole % on bleach) | Temp °C. | Lovibond colour Uncatalysed | Lovibond colour Catalysed | Total colour (5R + Y) Uncatalysed | Total colour (5R + Y) Catalysed |
|---|---|---|---|---|---|---|---|
| 45-minute intervals) | | | | | | | |
| 7.5 | 0.56 | | 50 | — | 4.4R 31Y | — | 53 |
| 7.5 (with addition of nickel palmitate to give 400ppm Ni) | 0.56 | | 50 | | 5R 26Y | — | 51 |

We claim:

1. In a process for bleaching a naturally occurring oil or fat containing a colored impurity, the improvement which comprises treating said oil or fat with an aqueous polar bleaching agent in an amount effective to convert said colored impurity to a substantially colorless product, in the presence of an effective amount of a phase transfer catalyst.

2. The process of claim 1, wherein the oil or fat is a vegetable or animal product selected from the group consisting of palm oil, coconut oil, rice bran oil, bay tree leaf oil, sal oil and tallow.

3. The process of claim 1, wherein the bleaching agent is an oxidative bleaching agent selected from the group consisting of hypochlorites, peroxides, peroxoacids and chlorites.

4. The process of claim 1, wherein the bleaching agent is used in an amount of from 0.5 to 10% by weight based on the oil or fat.

5. The process of claim 1, wherein the phase transfer catalyst is a quaternary ammonium compound.

6. The process of claim 5, wherein the phase transfer catalyst is a compound of the formula I:

$$R_1R_2R_3R_4N^+X^- \quad (I)$$

wherein $R_1$, $R_2$, $R_3$ and $R_4$ are alkyl groups each having from 1 to 22 carbon atoms, the total number of carbon atoms in all the R groups being not less than 16, and $X^-$ is a monovalent anion or 1/m of an m-valent anion.

7. The process of claim 5, wherein the phase transfer catalyst is a compound of the formula II:

$$R_5R_6R_7R_8N^+X^- \quad (II)$$

wherein $R_5$, $R_6$, $R_7$ and $R_8$ are alkyl groups each having from 4 to 22 carbon atoms, and $X^-$ is a monovalent anion or 1/m of an m-valent anion.

8. The process of claim 5, wherein the phase transfer catalyst is a compound of the formula III:

$$R_9R_{10}R_{11}R_{12}N^+X^- \quad (III)$$

wherein $R_9$ and $R_{10}$ are alkyl groups each having from 1 to 3 carbon atoms, $R_{11}$ and $R_{12}$ are alkyl groups each having from 10 to 22 carbon atoms, and $X^-$ is a monovalent anion or 1/m of an m-valent anion.

9. The process of claim 5, wherein the phase transfer catalyst is selected from tetra-n-octyl ammonium compounds, tetra-n-butyl ammonium compounds and di(hydrogenated tallow alkyl)dimethyl ammonium compounds.

10. The process of claim 1, wherein the phase transfer catalyst is used in an amount of from 0.2 to 10 mole % based on the bleaching agent.

11. In a process for bleaching an animal or vegetable oil or fat selected from the group consisting of palm oil, coconut oil, rice bran oil, bay tree leaf oil, sal oil and tallow, the improvement which comprises treating said oil or fat with from 0.5 to 10% by weight of a polar oxidative bleaching agent selected from the group consisting of hypochlorites, peroxides, peroxoacids and chlorites, in the presence of an effective amount of a cationic phase transfer catalyst.

12. In a process for bleaching palm oil, the improvement which comprises treating said palm oil with from 2 to 4.5% by weight of hypochlorite in the presence of an effective amount of a cationic phase transfer catalyst.

13. In a process for bleaching a vegetable oil selected from the group consisting of sal oil and rice bran oil, the improvement which comprises treating said oil with from 5 to 7.5% by weight of hypochlorite in the presence of an effective amount of a cationic phase transfer catalyst.

* * * * *